United States Patent [19]

Shannon et al.

[11] Patent Number: 5,073,294

[45] Date of Patent: Dec. 17, 1991

[54] PROCESS OF PREPARING COMPOSITIONS HAVING MULTIPLE ORIENTED MESOGENS

[75] Inventors: Paul J. Shannon, Exton, Pa.; Shao-Tang Sun, Newark; Brian J. Swetlin, Wilmington, both of Del.

[73] Assignee: Hercules Incorporated, Wilmington, Del.

[21] Appl. No.: 605,724

[22] Filed: Oct. 29, 1990

Related U.S. Application Data

[62] Division of Ser. No. 490,115, Mar. 7, 1990.

[51] Int. Cl.[5] .................. C09K 19/52; C09K 19/56; G02F 1/13
[52] U.S. Cl. ................. 252/299.01; 252/299.4; 359/76; 359/96; 359/103; 359/104; 359/106
[58] Field of Search ................. 252/299.01, 299.4; 350/350 S, 350 R, 349, 341

[56] References Cited

U.S. PATENT DOCUMENTS

| | | | |
|---|---|---|---|
| 4,637,896 | 1/1987 | Shannon | 252/299.7 |
| 4,758,447 | 7/1988 | Broer et al. | 427/44 |
| 4,796,980 | 1/1989 | Kaneko et al. | 350/350 |
| 4,893,907 | 1/1990 | Mallinson | 350/350 |
| 4,898,456 | 2/1990 | Okada et al. | 350/350 |
| 4,944,896 | 7/1990 | De Martino et al. | 252/299.01 |
| 4,948,532 | 8/1990 | De Martino et al. | 252/299.01 |
| 4,957,655 | 9/1990 | Khanarian et al. | 252/299.01 |
| 4,962,160 | 10/1990 | De Martino et al. | 252/299.01 |
| 4,974,941 | 12/1990 | Gibbons et al. | 350/349 |
| 4,983,318 | 1/1991 | Matsumoto et al. | 252/299.01 |

FOREIGN PATENT DOCUMENTS

| | | |
|---|---|---|
| 233667 | 8/1987 | European Pat. Off. . |
| 261712 | 3/1988 | European Pat. Off. . |
| 331233 | 9/1989 | European Pat. Off. . |
| 62-70406 | 3/1987 | Japan . |

OTHER PUBLICATIONS

Portugall et al.—Synthesis and Phase Behaviour of Liquid Crystalline Polyacrylates.
Sibaev et al.—Thermotropic Liquid-Crystalline Polymers-VI.
Wendorff et al.—Nonlinear Optical Phenomena in Liquid Crystalline Side Chain Polymers.

Primary Examiner—Robert L. Stoll
Assistant Examiner—Philip Tucker
Attorney, Agent, or Firm—Mark D. Kuller

[57] ABSTRACT

A liquid crystal polymer film or fiber comprising polymeric liquid crystals having aligned multiple oriented mesogens and a process for preparing such a polymeric liquid crystal film or fiber comprising aligning in a multi-oriented state a nematic or smectic monomeric mesophase (liquid crystal monomer) and photopolymerizing the mesophase, are disclosed. The film or fiber may be adhered to a substrate, part of a liquid crystal display cell, or a free standing polymeric film or fiber. According to a preferred process, the mesophase is aligned in a multi-oriented state using linearly polarized light.

24 Claims, 3 Drawing Sheets

PROCESS OF PREPARING COMPOSITIONS HAVING MULTIPLE ORIENTED MESOGENS

This is a divisional of U.S. patent application Ser. No. 07/490,115, filed Mar. 7, 1990.

This invention concerns liquid crystal polymer films and fibers having aligned multi-oriented mesogens (liquid crystal moieties) and processes for preparing such films and fibers.

BACKGROUND OF THE INVENTION

Liquid crystalline monomers and mixtures of monomers in combination with photoinitiators can exhibit nematic and smectic mesophases. Under ultraviolet ("UV") irradiation these nematic and smectic mesophases can undergo rapid photopolymerization, in the presence of UV-photoinitiators, to freeze-in the structure and orientation (alignment) of the nematic and smectic mesophases into a polymer matrix. The films and fibers derived from this process have valuable optical and physical properties and are useful as packaging films, laminated films, polarizing films, optical information storage films, optical fibers, etc.

Using conventional techniques, the mesophase is aligned on a substrate using standard aligning techniques for low molecular weight liquid crystals, such as rubbing the surface of a glass substrate or a polymer coating on a substrate, so that all of the molecules are oriented in one direction. After irradiation with UV light, the resulting polymer has the orientation of the monomeric mesophase film frozen into the polymer matrix.

For instance, Japanese 62 70,406 describes the polymerization of nematic monomers in the liquid crystalline state in the presence of a polymerization initiator with ultraviolet radiation. The molecules are oriented by a support or coating on a support, which support or coating has been previously rubbed with cloth in the orientation direction.

The instant inventors have discovered that orientation of monomeric liquid crystals can be selectively controlled to produce aligned multi-oriented monomeric mesophases and that these aligned multi-oriented mesophases can be photopolymerized to give films and fibers with multiple orientations frozen-in to polymeric matrices.

SUMMARY OF THE INVENTION

Accordingly, in one embodiment the invention is a liquid crystal polymer film or fiber comprising polymeric liquid crystals having aligned multiple oriented mesogens. The film or fiber may be adhered to a substrate, part of a liquid crystal display cell, or a free standing polymeric film or fiber.

In another embodiment, the invention is a process for preparing such a polymeric liquid crystal film or fiber comprising aligning in a multi-oriented state a nematic or smectic monomeric mesophase (liquid crystal monomer) and photopolymerizing the mesophase. According to a preferred process, the mesophase is aligned in a multi-oriented state using linearly polarized light.

DETAILED DESCRIPTION OF INVENTION

Figure 1:
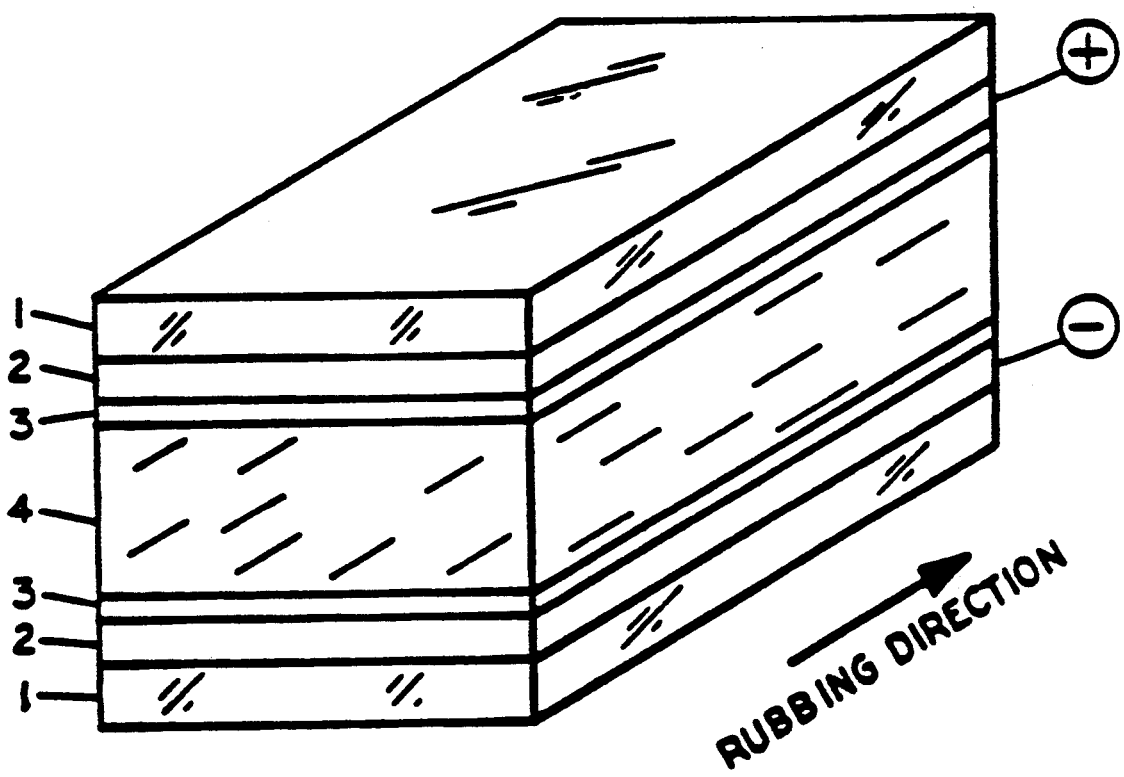
FIG. 1 is a schematic of a typical liquid crystal cell.

By "multiple orientation", "multi-oriented" or the like it is meant that the molecular axes of the mesogens (liquid crystal moities) are oriented in two or more directions in different regions of the film or fiber. Here, it should be understood that the direction of orientation is the average direction of an ensemble of mesogens which can be quantified by order parameter.

By "aligned multiple orientation", "aligned in a multi-oriented state" or the like it is meant that the orientations are not random, i.e., the mesogens are in two, three or more selected orientations. Most frequently the films or fibers will have two or three selected orientations. They may comprise homogeneous orientations, homeotropic orientations or combinations thereof.

The liquid crystal monomers useful in this invention exhibit smectic (e.g., smectic A or C) or nematic mesophases at or near room temperature by themselves, or in combination with other monomers, are capable of being polymerized by UV-initiated free-radical polymerization, and are capable of being aligned in predominately homeotropic or homogeneous orientations. Preferred are those that form polymers having the general formula:

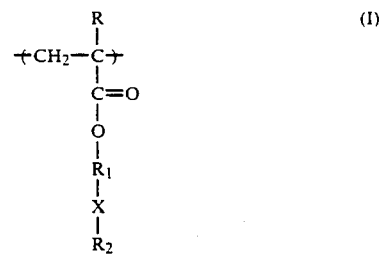

wherein R is a hydrogen or $CH_3$;

$R_1$ is a linear or branched $C_2$ to $C_{12}$ alkyl group which is uninterrupted or interrupted by one or more of the groups —O—, —S— or

X is —O—, —S— or

or a covalent bond; $R_3$ is a $C_1$ to $C_4$ alkyl group; $R_2$ is a radical of the formula:

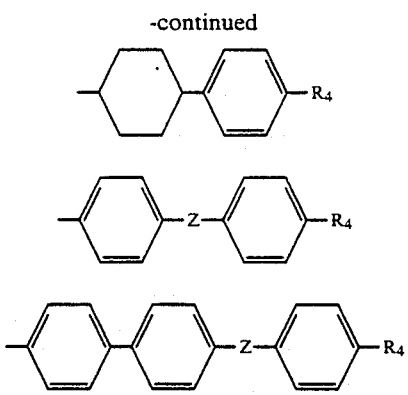

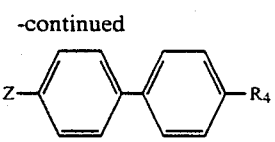

wherein Z is —CO—O—, —O—CO—, —CH=CH—, —N=CH— or —CH=N—; and $R_4$ is hydrogen, Cl, Br, F, nitro, nitrile, $C_1$ to $C_{12}$ straight chain or branched alkyl, $C_5$ to $C_7$ cycloalkyl, $C_1$ to $C_{12}$ straight chain or branched alkoxy, $C_1$ to $C_{12}$ straight chain or branched alkoxycarbonyl or straight chain or branched alkyl thiolyl.

Specific examples of monomers useful in this invention, shown below, are those derived from the families cyanobiphenyls (1), cyanophenyl benzoates (2), alkyloxyphenyl benzoates (3), biphenyl benzoates (4), alkyloxybiphenyl benzoates (5), cyanophenyl cyclohexanes (6) and cyanobiphenyl benzoates (7). In the following structures R is hydrogen or $CH_3$, n is 2 to 12 and R' is $C_1$ to $C_{12}$ straight chain or branched alkyl.

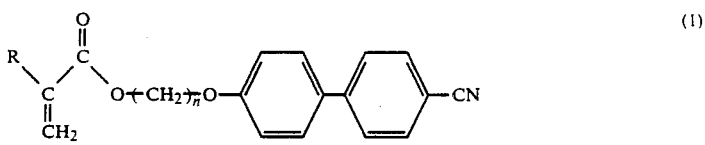

(1)

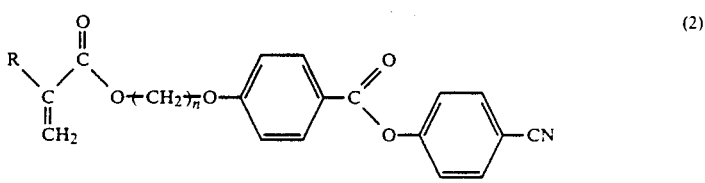

(2)

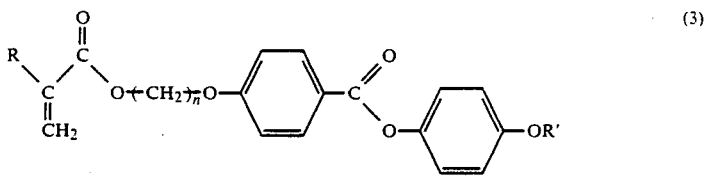

(3)

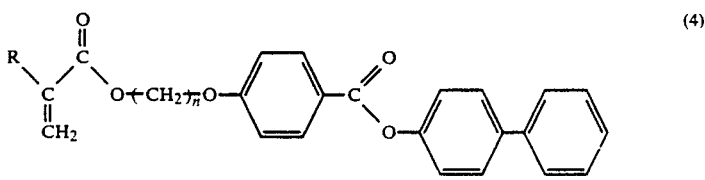

(4)

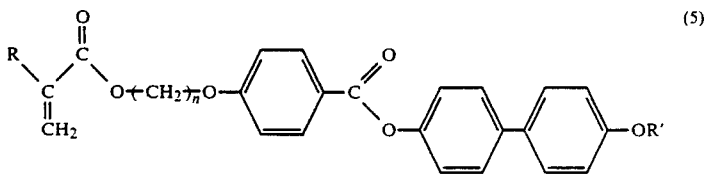

(5)

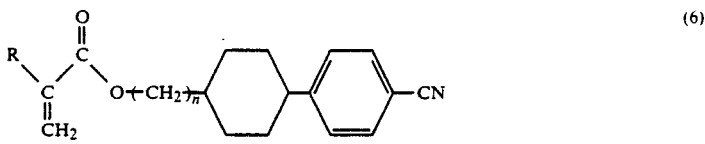

(6)

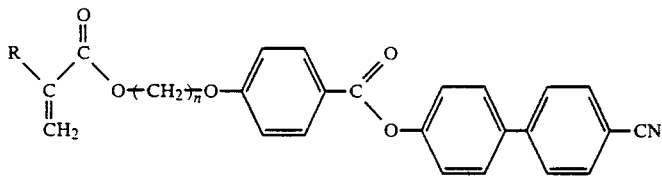

(7)

The synthesis of these monomers is known in the art. For instance, monomers of type 1 have been prepared by alkylation of 4'-(hydroxy)-4-cyanobiphenyl with omega-bromoalcohols followed by esterification of the alcohol with acryloyl or methacryloyl chloride. V. P. Shibaev, S. G. Kostromin and N. A. Plate, Eur. Polym. J., 18, 651 (1982).

Monomers 2, 3, 4, and 5 have been prepared by alkylation of 4-hydroxybenzoic acid with omega-chloroalcohols, esterification of the resulting alcohol with acrylic or methacrylic acid, conversion of the 4-substituted benzoic acid to an acid chloride and esterification of the acid chloride with 4-substituted phenols or 4'-substituted-4-hydroxybiphenyl. M. Portugal, H. Ringsdorf, R. Zentel, Makromol. Chem., 183, 2311 (1982).

Mixtures of these monomers, when melted, exhibit nematic or smectic mesophases when cooled to near room temperature. In many cases these mesophases are metastable and crystallization of one or more of the monomers occurs over a period of time, destroying the mesophase. The rate at which crystallization occurs varies widely. It is well known that a mixture of a variety of monomers tends to depress the tendency toward crystallization. Thus, in many cases nematic or smectic mesophases do not undergo crystallization for several hours to several days. In this period of time the mesophases have the properties of conventional low molecular weight nematic or smectic phases. As a result, these mesophases can be aligned and then polymerized.

Multifunctional monomers, useful as crosslinking agents, can be added to the monomeric liquid crystals if desired. Conventional crosslinking agents can be added generally at levels of about 0.5 to about 5 weight percent. These include hexanediol dimethacrylate and diacrylate, butanediol dimethacrylate and diacrylate, pentaerythritol triacrylate and trimethacrylate, ethylene glycol dimethacrylate and diacrylate, diethylene glycol dimetnacrylate and dimethacrylate, and triethylene glycol dimethacrylate and diacrylate. Liquid crystalline difunctional monomers also can be added to the monomeric liquid crystal at levels ranging from about 0.5 to about 30 weight percent. These materials include the liquid crystalline acrylates and methacrylates described in European Patent Application No. 261,712, U.S. Pat. No. 4,758,447 and U.S. Pat. No. 4,808,684.

According to this invention, polymeric films having aligned multi-oriented mesogens are made by photopolymerization of nematic or smectic monomers in aligned multi-oriented states. Photopolymerization is initiated by UV radiation.

A small amount of photoinitiator, preferably about 0.5 to about 2.0 weight %, is added to the polymerizable monomer composition to enhance the reactivity of the composition toward UV radiation. Examples of photoinitiators which will be useful to practice the present invention are benzophenone, 2,2-dimethoxy-2-phenylacetophenone, 2,2-diethoxyacetophenone, 2-benzoyloxyacetophenone, 2-chlorothioxanthone and 2-hydroxycyclohexyl phenyl ketone, all of said compounds being provided by way of illustration and not limitation.

Generally, photoinitiator is added to a pre-melted monomer mixture as a solid. The mixture is then reheated in the absence of UV light to dissolve the photoinitiator and then cooled to give the nematic or smectic mesophase.

The polymerizable smectic or nematic mesophases may be oriented using conventional techniques, such as electric or magnetic fields, surface alignment techniques (e.g., rubbing) or applying shear (e.g., extrusion). They may also be oriented by a new technique using linearly polarized light which is described by Gibbons et al in U.S. Pat. No. 4,974,941 (issuing on U.S. patent application Ser. No. 07/320,424, filed Mar. 8, 1989).

According to one conventional technique for obtaining a homogeneous orientation, the surface of a substrate (typically, glass or coated glass) is rubbed along a fixed linear direction with a cloth. By rubbing the surface, one preferentially alters the surface state so that generally the "long" molecular axis of the liquid crystal aligns along the rubbing direction. This orientation is transferred to the bulk of the liquid crystal medium via intermolecular forces.

Alignment of a nematic phase in a homogeneous orientation can be accomplished by treatment of a glass surface with a polyamide, polyimide or other coating, curing the coating, and buffing the cured coating with a polishing cloth. Equilibration of a nematic phase between such treated substrates results in a uniform homogeneous orientation. bands above about 400 nm are preferred. Some specific examples of dyes useful in the laser alignment of liquid crystals are listed in the following Table.

TABLE

| Dye Number | Structure | Peak Absorption Wavelength in Chloroform (nm) |
|---|---|---|
| 1 | $NH_2-\text{C}_6H_4-N=N-\text{C}_6H_3(CH_3)-N=N-\text{C}_6H_3(OCH_3)(CH_3)-N(H)-C_4H_9$ | 495 |

TABLE-continued

| Dye Number | Structure | Peak Absorption Wavelength in Chloroform (nm) |
|---|---|---|
| 2 | $NH_2-C_6H_4-N=N-C_6H_3(CH_3)-N=N-C_6H_2(OCH_3)(CH_3)-N(H)-C_{12}H_{25}$ | 499 |
| 3 | $C_2H_5-N(H)-C_{10}H_6-N=N-C_6H_4-N=N-C_6H_3(CH_3)-N=N-C_6H_2(OCH_3)(CH_3)-N=N-C_{10}H_6-N(H)-C_2H_5$ | 570 |
| 4 | 1,4-bis(4-ethylphenylamino)anthraquinone | 540 |
| 5 | $NH_2-C_6H_4-N=N-C_6H_3(CH_3)-N=N-C_6H_2(OCH_3)(CH_3)-NH_2$ | 460 |
| 6 | $NH_2-C_6H_4-N=N-C_6H_3(CH_3)-N=N-C_6H_2(OCH_3)(CH_3)-N(H)-C_6H_{13}$ | 499 |

The light source useful in laser alignment of liquid crystals must be linearly polarized. Further, the linearly polarized light must have a wavelength in the absorption band of the anisotropic absorbing molecules. Typically the light will be in the ultraviolet through the infrared range as the dyes will have peak absorption in this range. Preferably, the light will have a wavelength within the range of about 150 nm to about 2000 nm. The most preferred source of light is a laser, e.g., an argon, helium neon or helium cadmium laser. With lower power lasers it may be necessary to focus the light beam onto the substrate, but generally it is not necessary to focus the light beam.

There are two general approaches for performing laser alignment. The substrate containing the anisotropic absorbing material can be exposed to polarized light and then made to contact the polymerizable mesophase, or the polymerizable mesophase can be brought in contact with a substrate coated with an anisotropically absorbing material and then exposed to the polarized light. Both processes can be readily carried out with linearly polarized light having a wavelength higher than 400 nm. Exposure of polymerizable liquid crystals to UV light will normally initiate polymerization and, therefore, use of lower wavelengths is generally only useful with the first approach.

The process of laser alignment may be used to align a monomeric liquid crystal medium which is in a randomly aligned state to a homogeneous or homeotropic state or to realign a previously aligned (homogenous or homeotropic) liquid crystal medium. Best results are obtained with liquid crystal media of the type that will align homogeneously.

Laser alignment should be carried out with at least one substrate contacting the monomeric liquid crystal medium. However, the liquid crystal medium can form part of a cell having two such substrates, e.g., as shown in FIG. 1 (described below).

The linearly polarized light is applied to the entire medium that is to be aligned or a portion of a medium that is to be aligned. The light beam may be stationary or rotated. Exposure can be in one step, in bursts or by other methods. Exposure times vary widely with the materials used, and other predictable factors, and can range from less than one second to over an hour. The anisotropic absorbing molecules and the liquid crystal monomers are rotated and, as a result, the projection of the liquid crystal monomers on the substrate(s) assumes an angle + and − theta with respect to the direction of the linear polarization of the incident light beam.

After the laser alignment process is completed the liquid crystal medium has "memory", i.e., it will maintain the alignment which is induced by the linearly polarized light source. (The anisotropic medium can, of course, be realigned to the original or a third alignment by this process.)

The effects of the laser alignment process can be observed using two polarizers. That is, when white light is applied to a cell having a polarizer on each side one observes a color change in the exposed region relative to the background which indicates a change in the angular position of the liquid crystal monomers and, thus, a change in the birefringence of the cell. Results are sensitive to the exposure time; intensity, wavelength and direction of the linearly polarized light; sample temperature; liquid crystal monomers used and their concentrations; amount(s) and properties of the anisotropically absorbing molecules; etc.

It is not necessary to use conventional alignment layers, such as buffed alignment layers, in the laser alignment process. However, in many instances performance is improved with a buffed or rubbed alignment layer. Other orientation layers and techniques may also be used with the laser alignment process.

In the process of this invention, the second, third, etc., orientations are induced simultaneously or subsequent to inducement of a first alignment. All of the previously described techniques are useful for inducing these orientations. Preferably, a first orientation is induced by surface alignment and other orientations are induced by other techniques, most preferably laser alignment.

The process may be carried out by first inducing alignment in one direction using surface techniques and, then, inducing a second alignment by applying a voltage to selected areas of the material. Liquid crystal cells useful in this technique are fabricated with conducting layers in selected areas, according to conventional techniques. For example, such a cell may be sequentially buffed to give a preferred homogeneous orientation of monomeric liquid crystals, filled with a monomeric polymerizable mesophase possessing positive dielectric anisotropy, and aligned in selected areas by applying a voltage. The areas having had voltage applied will be predominately oriented in a homeotropic manner and the other areas will be predominately oriented in a homogeneous manner.

A schematic of a cell useful for this embodiment is shown in FIG. 1. This schematic is exemplary and not intended to be limiting. The cell contains a liquid crystal medium (4). The mesogens are represented by short lines. The cell comprises two substrates (1) made of glass coated with a transparent conductive coating (e.g., indium-tin-oxide) (2). The conductive coating is shown as having been applied over the entire surface area of the cell, but for this embodiment is only applied over the portions of the cell where an orientation other than that of the rubbing direction is desired. Coated over the conducting layers and glass are thin films of organic material (3) (e.g., polyimide), which in this case has been rubbed in a linear fashion with a buffing cloth (known as an "aligning layer"). The coated substrates are sandwiched together (aligning layers facing inward) with small glass fibers having diameters of from about 2–20 micrometers (not shown in the Figure) used to control the spacing. The liquid crystal layer (4) is sealed with, for example, epoxy (not shown). The $\oplus$ and $\ominus$ shown in the Figure represent applied voltage (the indicated voltage direction in this Figure is not intended to be limiting).

In a like manner a mesophase possessing positive magnetic anisotropy can be oriented in a homeotropic orientation using a magnetic field. If a cell is buffed to give a preferred homogeneous orientation of monomeric liquid crystals, the cell filled with a monomeric polymerizable mesophase possessing positive magnetic anisotropy, and the cell exposed in selected areas to a magnetic field oriented perpendicular to the plane of the cell, an aligned multi-oriented monomeric phase will be obtained. The areas within the magnetic field will be oriented predominately in a homeotropic orientation and the areas not influenced by the magnetic field will remain in the homogeneous orientation.

According to the preferred process, surface alignment is used to align the liquid crystal monomers. Laser alignment or other techniques may be used to enhance this alignment. Then, laser alignment is used to induce alignment in a second, third, or other orientation.

Figure 3:
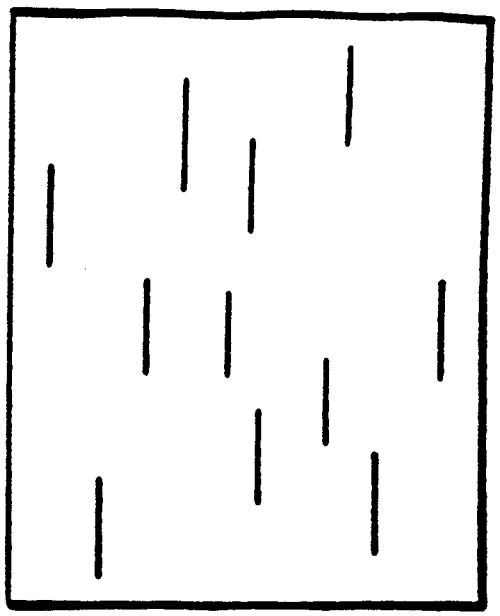
FIG. 3 is a front view of a liquid crystal medium which has been aligned by rubbing.
Figure 4:
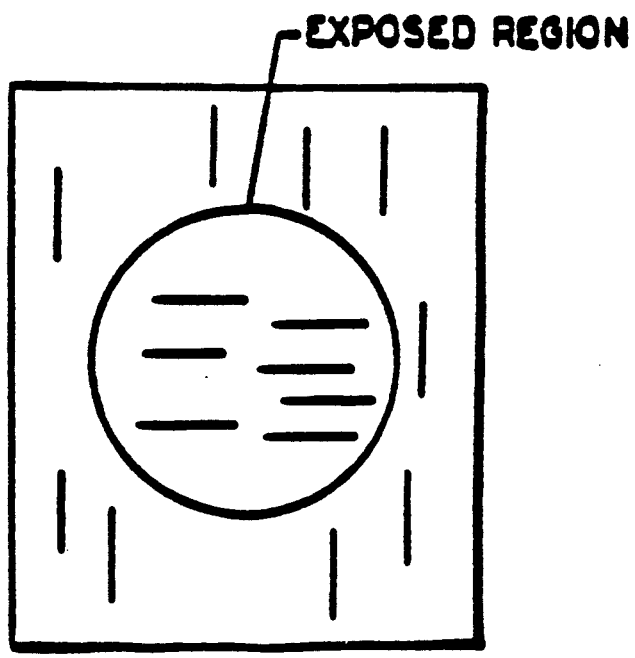
FIG. 4 is a front view of the liquid crystal medium of FIG. 3 after it has been aligned in a multi-oriented manner.

FIG. 3 shows a liquid crystal medium which has been aligned in one direction. FIG. 4 shows an example where a region of the medium has been oriented using laser alignment. This Figure illustrates the case where the liquid crystal molecules have been rotated 90 degrees to both the incident light polarization and the original alignment direction.

There are numerous other ways to achieve aligned multi-oriented mesophases. A substrate (or both substrates of a cell) may be rubbed or buffed in different directions in various regions. A substrate (or substrates) may be rubbed or buffed so as to induce a homogeneous alignment and then a region(s) of the substrate may be coated with a surface active agent, such as n-octadecyldimethyl 3-(trimethoxysilyl) propyl ammonium chloride, which will induce a homeotropic alignment in the coated regions. The skilled artisan will recognize many other variations.

Once the desired aligned multi-oriented mesophase has been achieved, it can be fixed in as polymer matrix by exposing the mesophase to UV light at, or near, room temperature. Preferably the UV polymerization is conducted between 15° and 40° C. The way in which the photopolymerization is achieved may have an effect on the optical characteristics of the resulting polymer. Thus, where optical properties duplicating the monomer phase are desired, it appears desirable to used a high intensity light source which induces rapid polymerization. On the other hand, slower polymerization induced by lower intensity light may tend to produce polymeric films and fibers which have lower transmission characteristics.

Aligned multi-oriented films may also be produced according to the present invention by sequential photopolymerization of the monomeric materials. For example, the different orientations exhibited by liquid crystals which exhibit phase sequences of isotropic-nematic-smectic can be imparted to a film by first orienting the mesophases at one temperature and, using a mask to block certain regions, irradiating the mesophase to fix the orientation in the other regions (the exposed areas). By removing the mask and changing the temperature of the partially cured material so that the uncured regions enter a different orientation, upon subsequent irradiation the second orientation can be fixed. This technique may be extended to provide films having multiple orientations in any desired pattern and may be used in conjunction with the techniques described above.

While the process of this invention is directed to aligning liquid crystal monomers prior to polymerization, additional orientations may be induced after polymerization, for instance by using linearly polarized light to realign mesogens or heating the polymers or regions thereof.

The films and fibers of this invention are useful as high resolution imaging films, packaging films, filtration membranes, laminated films, polarizing films, optical information storage films, waveguide devices, optical fibers, etc., wherein the aligned multi-oriented mesogens will provide advantages over similar films and fibers which are aligned in a single orientation. These films and fibers offer a high degree of control over the refractive index in areas selected by the artisan. Periodic variations of spatial refractive indices make these films and fibers especially useful in optical communications. The films and fibers offer a high degree of optical transparency not found in other liquid crystal materials. Aligned multi-oriented films and fibers also have unique mechanical properties derived from controlled orientation of the mesogens in these polymers. Films and fibers prepared using the laser alignment process are especially useful because of their high resolution of orientation.

This invention is demonstrated in the following examples, which are illustrative and not intended to be limiting, wherein all percentages, are by weight.

EXAMPLE 1

This example illustrates the formation of 4'-(6-bromohexyloxy)-4-cyanobiphenyl, an intermediate used in the synthesis of monomer 1a.

A mixture of 4'-hydroxy-4-cyanobiphenyl (7.8 g, 40 mmol), potassium carbonate (8.3 g, 60 mmol), 1,6-dibromohexane (29.8 g, 120 mmol), and acetone (80 milliliters ("mL")) was heated to reflux for 6 hours ("h") under a nitrogen atmosphere. The acetone was concentrated and the residue dissolved in ether-dichloromethane (4:1, 400 mL). The solution was filtered through glass fiber. The filtrate was washed with water and brine, dried over magnesium sulfate, and concentrated. Excess 1,6-dibromohexane was removed by Kugelrohr distillation up to 75° C. at 0.1 mm Hg. The material remaining in the pot was recrystallized from ethanol (100 mL), filtered while hot, and cooled in the freezer to give crystals of the bromide (9.6 g, 67%): melting point ("mp") 65.5°–66° C., mesophase at 63° C. in cooling; NMR (CDCl$_3$) 7.55(s, 4H), 7.49(d, 2H), 6.82(d, 2H), 3.91(t, 2H), 2.0–1.3(m, 8H); IR (CH$_2$Cl$_2$) 2222, 1602 cm$^{-1}$.

EXAMPLE 2

This example illustrates the formation of 4'-(8-bromooctyloxy)-4-cyanobiphenyl, an intermediate in the synthesis of monomer 1b.

Treatment of 4'-hydroxy-4-cyanobiphenyl with 1,8-dibromooctane as described in example 1 gave crystals of the bromide (10.9 g, 69%): mp 79°–80° C.; NMR (CDCl$_3$) 7.55(s, 4H), 7.50(d, 2H), 6.85(d, 2H), 3.9(t, 2H), 3.35(t, 2H), 1.9–1.3(m, 12H).

EXAMPLE 3

This example illustrates the formation of 4'-(10-bromodecyloxy)-4-cyanobiphenyl, an intermediate in the synthesis of monomer 1c.

Treatment of 4'-hydroxy-4-cyanobiphenyl with 1,10-dibromodecane as described in Example 1 gave crystals of the bromide (13.0 g, 78%): mp 69°–71° C.; NMR (CDCl$_3$) 7.6(s, 4H), 7.5(d, 2H), 6.9(d, 2H), 3.95(t, 2H), 3.35(t, 2H), 1.95–1.3(m, 16H); IR (KBr) 2238, 2222, 1605 cm$^{-1}$.

EXAMPLE 4

This example illustrates the formation of methacrylate monomer 1a.

A mixture of 4'-(6-bromohexyloxy)-4-cyanobiphenyl (7.0 g, 20 mmol), prepared as described in Example 1; potassium methacrylate (4.8 g, 40 mmol), hydroquinone (10 mg), and distilled dimethylformamide (40 mL) was heated to 70°–80° C. for 3 h. The mixture was diluted with water (200 mL) and extracted with ether-dichloromethane (4:1, 200 mL portions, 2 times). The extract was washed with water, dried over magnesium sulfate, and concentrated. The resulting solid was recrystallized from absolute ethanol (90 mL), filtered and cooled in the freezer to obtain crystals of 1a (5.5 g, 76%): mp 74°–76° C.; NMR (CDCl$_3$) 7.55(s, 4H), 7.45(d, 2H), 6.88(d, 2H), 6.0(s, 1H), 5.45(s, 1H), 1.95–1.3(m, 11H); IR (KBr) 2225, 1708 cm$^{-1}$.

EXAMPLE 5

This example illustrates the formation of methacrylate monomer 1b.

The bromide described in Example 2 was treated with potassium methacrylate as described in Example 4 to give 1b as crystals (4.9 g, 63%): mp 71°–73° C.; NMR (CDCl$_3$) 7.6(s, 4H), 7.48(d, 2H), 6.9(d, 2H), 6.03(s, 1H), 5.5(s, 1H), 4.02(m, 4H), 2.0–1.3(m, 12H).

EXAMPLE 6

This example illustrates the formation of methacrylate monomer 1c.

The bromide described in Example 3 was treated with potassium methacrylate as described in Example 4 to give 1c as crystals (5.9 g, 66%): mp 69°–70° C., mesophase 47° C. in cooling cycle; NMR (CDCl$_3$) 7.53(s, 4H), 7.4(d, 2H), 6.85(d, 2H), 5.95(s, 1H), 5.45(s, 1H), 4.0(m, 4H), 2.0–1.3(m, 19H).

EXAMPLE 7

This example illustrates the formation of 4-(10-hydroxydecyloxy)benzoic acid, an intermediate in the formation of monomer 2a.

A mixture of 4-hydroxybenzoic acid (69.0 g, 0.5 mol), 10-chloro-1-decanol (106 g, 0.55 mol), potassium hydroxide (75 g, 1.15 mol), potassium iodide (0.1 g), and absolute ethanol (300 mL) was heated to reflux with mechanical stirring for 18 h. The mixture was diluted with water (800 mL) and stirred 0.5 h at room temperature. The mixture was acidified with 12N hydrochloric acid (125 mL) and the mixture stirred for 5 h. The material was allowed to sit overnight and filtered. The solid was washed with water and air dried 4 days. The solid was recrystallized from tetrahydrofuran (300 mL) to give 4-(10-hydroxydecyloxy)benzoic acid (85.2 g, 58%): mp 115°–117° C.; NMR (CDCl$_3$+d$_6$ DMSO) 7.93(d, 2H), 6.85(d, 2H), 4.0(t, 2H), 3.52(t, 2H), 3.48(bs, 1H), 1.9–1.2(m, 16H).

EXAMPLE 8

This example illustrates the formation of 4-(10-methacryloyloxydecyloxy)benzoic acid, an intermediate in the preparation of monomer 2a.

A mixture of 4-(10-hydroxydecyloxy)benzoic acid (11.75 g, 40 mmol, prepared as described in Example 7), methacrylic acid (34.4 g, 0.4 mol), hexane (90 mL), toluene (130 mL), p-toluene sulfonic acid (1.0 g), and hydroquinone (0.2 g) was refluxed in a Dean-Stark apparatus for 4.5 h. The mixture was cooled to room temperature and insoluble solids were filtered off. The filtrate was washed several times with water (1 L total), dried over magnesium sulfate and concentrated. The excess methacrylic acid was removed by Kugelrohr distillation up to 70° C. at 0.1 mm Hg. The remaining residue was dissolved in tetrahydrofuran (40 mL) and diluted with hexane (300 mL). A small amount of insoluble material was filtered off and the solution cooled to give a white solid (6.5 g, mp 62°–102° C.). Column chromatography (silica gel; hexane:ethyl acetate, 4:1) gave a purified sample (5.2 g, 36%): mp 61°–103° C., smectic mesophase in the cooling cycle, 103° C.; NMR (CDCl$_3$) 9.45(bs, 1H), 8.03(d, 2H), 6.9(d, 2H), 6.03(s, 1H), 5.5(s, 1H), 4.1(t, 2H), 3.97(t, 2H), 1.9(s, 3H), 1.8–1.2(m, 16H).

EXAMPLE 9

This example illustrates the formation of monomer 2a.

A solution of 4-(10-methacryloyloxydecyloxy)benzoic acid (3.62 g, 10 mmol) in toluene (30 mL) was stirred with oxalyl chloride (15 mmol, 1.91 g) and 1 drop of dimethylformamide for 3 h at room temperature. Excess oxalyl chloride and toluene (10 mL) were distilled under reduced pressure. To the acid chloride solution sequentially was added 4-cyanophenol (1.43 g, 12 mmol), dichloromethane (10 mL) and triethylamine (21 mmol). The mixture was heated to 60°–65° C. in an oil bath for 1 h. The mixture was cooled, diluted with ether (150 mL) and washed with 1N hydrochloric acid, water and brine. The ether solution was dried over magnesium sulfate, concentrated, and recrystallized from ethanol to give a solid (3.90 g). Further purification by column chromatography (silica, hexane-ether; 4:1) and recrystallization from ethanol gave monomer 2a (3.6 g, 78%): mp 59.5°–59.7° C., crystallized in the cooling cycle at 53° C.; NMR (CDCl$_3$) 8.03(d, 2H), 7.62(d, 2H), 7.25(d, 2H), 6.88(d, 2H), 6.0(s, 1H), 5.45(s, 1H), 4.2–3.9(m, 4H), 1.9(s, 3H), 1.8–1.2(m, 16H); IR (KBr) 2225, 1730, 1720, 1712, 1640, 1603 cm$^{-1}$.

EXAMPLE 10

This example illustrates the formation of 4-(6-hydroxyhexyloxy)benzoic acid, an intermediate in the preparation of monomer 2b.

A mixture of 4-hydroxybenzoic acid (138 g, 1.0 mol) and 6-chloro-1-hexanol (150 g, 1.1 m01) was treated as described in Example 7 to give a solid (101.2 g, mp 127°–132° C.). Recrystallization of a portion of the solid from tetrahydrofuran gave pure 4-(6-hydroxyhexyloxy)benzoic acid: mp 132°–135° C.

EXAMPLE 11

This example illustrates the formation of 4-(6-methacryloyloxyhexyloxy)benzoic acid, an intermediate in the preparation of monomer 2b.

A solution of 4-(6-hydroxyhexyloxy)benzoic acid (24.0 g, 0.10 mol, prepared as described in Example 10) was treated with methacrylic acid as described in Example 8 to give 4-(6-methacryloylhexyloxy)benzoic acid after recrystallization from tetrahydrofuran-hexane (1:2) (19.9 g, 67%): mp 81°–94° C., nematic mesophase; NMR (CDCl$_3$) 9.82(bs, 1H), 8.0(d, 2H), 6.87(d, 2H), 6.05(s, 1H), 4.15(t, 2H), 4.0(t, 2H), 1.9(s, 3H), 1.85(m, 8H).

EXAMPLE 12

This example illustrates the preparation of monomer 2b.

A solution of 4-(6-methacryloyloxyhexyloxy)benzoic acid (8.9 g, 30 mmol, prepared as described in Example 11) was treated as described in Example 9 to give a white solid (6.75 g, 55%, mp 54°–57° C.). Further purification by silica gel chromatography (hexane-ether, 3:1) and recrystallization from ethanol gave pure monomer 2b: mp 64.3°–65.3° C.; nematic phase in cooling cycle, 40.2° C.; NMR (CDCl$_3$) 8.05(d, 2H), 7.67(d, 2H), 7.28(d, 2H), 6.90(d, 2H), 6.02(s, 1H), 5.5(s, 1H), 4.25–3.9(m, 4H), 1.9(s, 3), 1.85–1.30(m, 8H); IR (CHCl$_3$) 2225, 1738, 1715, 1635, 1600 cm$^{-1}$.

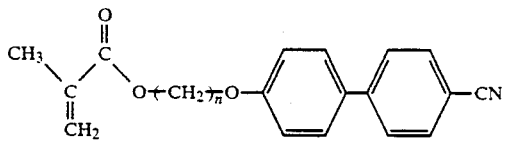

TABLE 1

| Example | Compound No. | n | Melting Point (°C.) |
|---------|--------------|----|---------------------|
| 4 | 1a | 6 | 74–76 |
| 5 | 1b | 8 | 71–73 |
| 6 | 1c | 10 | 69–70 |
|   |    |    | (47.0 nematic) |

Number in parenthesis refers to the cooling cycle.

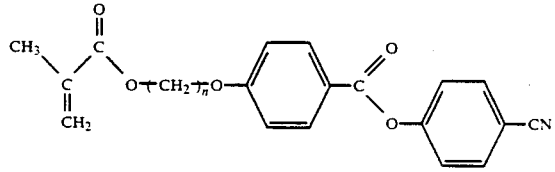

TABLE 2

| Example | Compound No. | n | Melting Point (°C.) |
|---------|--------------|----|---------------------|
| 9 | 2a | 10 | 59.5–59.7 |
| 12 | 2b | 6 | 64.3–65.3 |
|    |    |   | (40.2 nematic) |

EXAMPLE 13

This example illustrates the preparation of monomer 4.

4-(6-Methacryloyloxyhexyloxy)benzoic acid (15.3 g, 50 mmol) was treated with oxalyl chloride and 4-phenylphenol as described in Example 12 to give a white solid that was recrystallized from ethyl acetate-hexane to give 4 (14.4 g, 63%): mp 66.6° C., smectic phase to 72.2° C., nematic phase to 90.2° C.; NMR (CDCl$_3$) 8.26–7.9 (m, 2H), 7.65–7.05(m, 9H), 6.96–6.7(m, 2H), 6.01(s, 1H), 5.43(s, 1H), 4.06(t, 2H), 3.86(t, 2H), 1.9(s, 3H), 1.8–1.2(m, 8H).

EXAMPLE 14

This example illustrates the preparation of monomer 3.

4-(6-Methacryloyloxyhexyloxy)benzoic acid (15.3 g, 50 mmol) was treated with oxalyl chloride and 4-methoxyphenol as described in Example 12 to give a white solid that was recrystallized from ethyl acetate hexane to give 3 (10.9 g, 53%); mp 46° C., nematic phase evident in the cooling cycle at 44° C.; NMR (CDCl$_3$) 8.2–7.9(m, 2H), 7.23–6.65(m, 6H), 6.0(s, 1H), 5.45(s, 1H), 4.26–3.82(2t, 4H), 3.39(s, 3H), 1.9(s, 3H), 1.86–1.3(m, 8H).

EXAMPLE 15

This example illustrates the formation of the difunctional monomer useful as crosslinker with the liquid crystal monomers of this invention.

4-(6-Methacryloyloxyhexyloxy)benzoic acid (9.19 g, 30 mmol) was treated with oxalyl chloride and hydroquinone (1.48 g, 13 mmol) as described in Example 12 to give a white solid (7.28 g, 81%): mp 63.0° C., smectic mesophase to 83.7° C. and nematic mesophase to 137.7° C.; NMR (CDCl₃) 8.9-8.16(m, 4H), 7.36-6.9(m, 8H), 5.94(s, 2H), 5.56(s, 2H), 4.20-3.8(m, 8H), 1.84(s, 6H), 1.8-1.16(m, 16H).

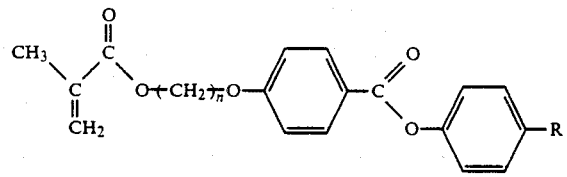

TABLE 3

| Example | Compound No. | n | R | Melting Point (°C.) |
|---|---|---|---|---|
| 13 | 4 | 6 | phenyl | 66.6 S 72.2 N 90.2 I* |
| 14 | 3 | 6 | OCH₃ | 46.0° C. (44.0 nematic)** |
| 15 | 5 | 6 | 4-methoxy-phenyl | — |

*S = smectic, N = nematic, I = isotropic.
**Number in parenthesis refers to the cooling cycle.

EXAMPLE 16

This example illustrates the mixing of monomers to obtain formulations exhibiting homeotropic nematic mesophases.

Monomers 1a (45 mg) and 1c (45 mg) were mixed and melted in a hot air stream to give a nematic fluid. A sample of this mixture was prepared between a microscope slide and a cover slip and heated above the isotropic point in a Mettler FP5 hotstage using a Mettler FP52 temperature control. The sample was cooled at 3° C. per minute. Nematic phase was evident from 43.8° C. to room temperature. The nematic phase crystallizes over a period of about 1 day at room temperature.

EXAMPLE 17

This example further illustrates the mixing of monomers to obtain homeotropic nematic mesophases.

Monomers 1a (90 mg), 1b (90 mg) and 1c (90 mg) were mixed and melted to give a nematic fluid. A sample of this material exhibited a nematic phase in the cooling cycle from 43.0° C. to room temperature. The sample crystallized over a period of about 2 days at room temperature.

EXAMPLE 18

This example further illustrates the mixing of monomers to obtain homeotropic nematic mesophases.

Monomers 2a (102 mg) and 2b (102 mg) were mixed and melted to give a nematic fluid that exhibited a nematic phase in the cooling cycle from 44.0° C. to room temperature. The material crystallized over a period of one day at room temperature.

EXAMPLE 19

This example illustrates the effect of added photoinitiator on the nematic mesophase temperature range.

2,2-Dimethoxy-2-phenylacetophenone (Irgacure 651, Ciba-Giegy, Ardsley, N.Y.) (5 mg, 2.5 wt %) was added to the mixture described in Example 18. The mixture was heated to make a homogeneous mixture. The mixture exhibited a nematic phase in the cooling cycle from 36.5° C. to room temperature. The material crystallized over a period of about 1 day at room temperature.

EXAMPLE 20

This example illustrates the alignment of a nematic phase in a homeotropic orientation.

Glass microscope slides were cleaned by sonicating 0.5 h in a 50:50 mixture of RBS-35 nonionic surfactant (Pierce Chemical Co., Rockford, Ill., 61105) and deionized distilled water, followed by sequential sonication for 0.5 h (each) with acetone, methanol, and deionized distilled water.

The nematic monomer composition described in Example 17 was placed on a cleaned glass microscope slide. The sample was sandwiched with a second clean slide by using 10 micron glass fiber spacers. The sample was allowed to rest undisturbed for about 5 minutes to allow a uniform homeotropic orientation to form.

EXAMPLE 21

This example further illustrates the alignment of a nematic monomer phase in a homeotropic orientation.

Glass slides that were cleaned as described in Example 20, were spin coated with a 1 wt % solution of n-octadecyldimethyl 3-(trimethoxysilyl)propyl ammonium chloride (Petrarch Inc., Bristol, Pa.) in methanol at 3000 RPMS for 1 minute. The coated plates were cured for 1 hr at 100° C. Thin cells were made from the coated plates by sandwiching 10 micron glass fiber spacers between two coated plates and sealing the plates together using a fast setting epoxy. Two holes, at opposite ends of the cell, were left in the epoxy seal to allow materials to be capillary filled. The cell was then warmed to 50°-60° C. with a heat gun and a small sample of the nematic composition described in Example 17 was placed at one of the filling holes in the cell. The cell quickly filled by capillary action. After the cell was filled, the sample was cooled to room temperature and allowed to rest undisturbed for several minutes to allow a uniform homeotropic orientation to form.

EXAMPLE 22

This example illustrates the alignment of a nematic monomer phase in a homogeneous orientation.

Glass plates, cleaned as described in Example 20, are spin coated with a 1 wt % solution of silicon polyimide (General Electric, SPI-1000) in 1-methyl-2-pyrrolidinone. The coated plates were cured for 1 hr at 100° C. and 2 hr at 225° C. The coated surface of the plates were buffed with a polishing cloth. Two treated plates were sandwiched together, sealed, and filled, as described in the last example. The cells were allowed to sit at room temperature to form a homogeneous orientation.

EXAMPLE 23

This example further illustrates the alignment of a nematic monomer phase in the homogeneous orientation.

Glass slides, cleaned as described in Example 20, were spin coated with a 1 wt % solution of Nylon Elvamide (E. I. Dupont de Nemours and Company, Wilmington, Del.) in methanol. The coated glass was heated to 100° C. for 1 hr. The coated glass plates were buffed with a polishing cloth. Two glass plates were then sandwiched together, sealed, and filled with nematic monomer as described in Example 22. The cells were allowed to sit at room temperature to develop a uniform homogeneous orientation.

EXAMPLE 24

This example illustrates the polymerization of a nematic monomer mesophase in a homeotropic orientation to give a polymer phase exhibiting the same orientation.

A cell was prepared as in Example 20. To the nematic monomer mixture described in Example 17 was added 1 wt % of Irgacure 651. The cell was filled with this monomer mixture at 50°-60° C. while shielding the cell from light. The cell was cooled to room temperature and allowed to sit to develop uniform homeotropic orientation. The sample was then exposed to UV light (200 watt Hg arc, 6-9 inches from the source) for 1 minute. A frozen homeotropic orientation was obtained. The cell was opened to give a free standing film.

EXAMPLE 25

This example illustrates the formation of polymer film exhibiting a homogeneous orientation.

A cell was prepared as described in Example 22. To the nematic monomer mixture described in Example 17 was added 1 wt % Irgacure 651. The cell was filled with this mixture at 50°-60° C. while shielding from light. The cell was allowed to sit to form a homogeneous orientation. The cell was irradiated with UV light (200 watt Hg arc, 6-9 inches from source) for 1 minute. The cell exhibited a frozen homogeneous orientation. A free-standing film was obtained upon opening the cell.

EXAMPLE 26

This example illustrates the alignment of a nematic monomer in a homeotropic orientation using an electric field.

Indium-tin oxide coated glass plates were precleaned as described in Example 20 and then coated with a 12.5 wt % of silicon polyimide as described in Example 22. On top of the polyimide layer was coated a thin layer of n-octadecyldimethyl 3-(trimethoxysilyl)propyl ammonium chloride in methanol as described in Example 21. Cells were prepared from the treated glass plates as described in Example 21. A slight overlap of the glass plates was allowed in sandwiching the glass plates to allow attachment of wire leads. Wires were attached to the exposed indium tin oxide coatings using a conductive epoxy to provide electrical contact. The cell was filled with the monomer composition used in the previous Example. An AC voltage of 30 VAC; square wave; 1 KHz was applied to the cell. A highly uniform homeotropic alignment was obtained. With the poling field still on, the sample was exposed to UV light (200 watt Hg arc) for about 1 minute. The homeotropic orientation was frozen into the polymer matrix. When the cell was opened a free-standing polymer film was obtained that exhibited a highly uniform homeotropic alignment.

EXAMPLE 27

This example illustrates the preparation of a multi-oriented polymer film using laser alignment to selectively orient a polymerizable monomer mixture followed by photopolymerization.

To a solution of 5 wt % silicone-polyimide in 1-methyl-2-pyrrolidinone was added 2.5 wt % of the dichroic bisazo dye 5 (shown in the Table in the specification). The solution was filtered through a 0.45 micron teflon membrane and spin coated onto pre-cleaned glass substrates (3000 revolutions per minute for 1 minute, after a 2 minute residence time). The coated plates were cured at 100° C. for 1 hour and 225° C. for 2 hours. The plates were buffed with a polishing cloth by moving the plates twice along the cloth parallel to the long axis of the glass. Next, 11 micron glass fibers were placed on one piece of the coated glass substrate and the other coated glass substrate was sandwiched on top of it (the coatings were on the inside of the resultant cell). The two pieces were pressed to an 11 micron spacing using clamps, epoxy was applied along the edges and the epoxy was cured for 5 minutes. Two spaces on opposite edges of the cell were left unsealed.

Figure 2:
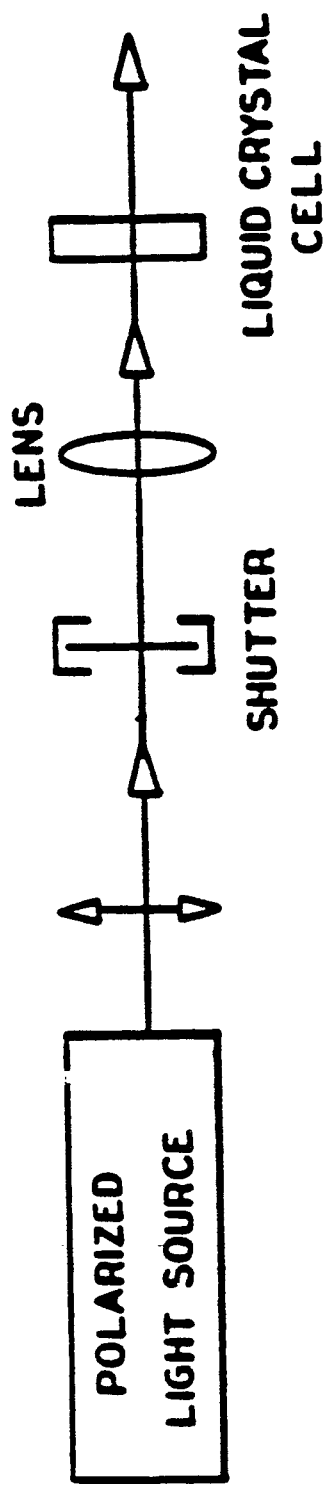
FIG. 2 shows an apparatus useful for aligning or realigning liquid crystal media using linearly polarized light.

Before the cell was filled with liquid crystal, it was exposed to light with the system described in FIG. 2 (with two lenses in sequence). The polarized light source was an argon laser (Model No. 2020-03, Spectra-Physics, Piscataway, N.J.) having a maximum power of approximately 1.2 watts at 514.5 nm wavelength. The laser was polarized vertically, as indicated by the two headed arrow in FIG. 2. The laser light was incident on a variable camera shutter to control the exposure time on the sample. When the shutter was opened, a laser light beam of 4 mm diameter passed through. It was expanded to 1 cm using the lenses. The laser beam was incident perpendicular to the plane of the glass substrate as indicated in FIG. 2. The incident light polarization was parallel to the linear rubbing direction of the cell.

On the empty cell was mounted a polyester photomask which had an image formed by a black ink (areas not to be exposed to light are covered by the black image areas). The cell was mounted on an optical bench so that the buffing direction was vertical. The cell was illuminated with a laser beam (1 cm in diameter, 514.5 nm) with vertical polarization of the light for 1 minute. The laser power was about 0.85 Watts. The cell was removed from the mount, warmed to about 60° C. and filled with the liquid crystal monomer mixture described in Example 24 at 1 atmosphere pressure by capillary action. The sample was cooled to room temperature and allowed to sit undisturbed for several minutes. The sample was protected from ambient UV light during the above procedure. After the alignment formed, the image of the mask was apparent in the cell. The illuminated areas were oriented perpendicular to the buffing direction whereas the masked areas retain their original alignment parallel to the buffing direction. This contrast in alignment was apparent when the sample was viewed between crossed polarizers.

The cell was then placed under a black lamp UV source for 1 minute to effect photopolymerization of the nematic phase. After polymerization, two distinct alignment orientations of the liquid crystal remained intact in the polymer film.

What is claimed is:

1. A process for preparing a composition in the form of a film or fiber, which process comprises aligning in a multi-oriented state a nematic or smectic monomeric mesophase and photopolymerizing the mesophase into a polymeric film or fiber having mesogens in one region aligned with their molecular axes oriented in a different direction than the mesogens aligned in at least one other region, wherein the orientation of the mesogens in at least one of the corresponding regions of the monomeric mesophase is induced by linearly polarized light.

2. The process of claim 1 wherein the resulting composition is in the form of a film.

3. The process of claim 1 wherein the resulting composition is in the form of a fiber.

4. The process of claim 1 wherein the linearly polarized light is laser light having a wavelength within the range of about 400 nm to about 2000 nm.

5. The process of claim 1 wherein the photopolymerizing is initiated by ultraviolet radiation and the monomeric mesophase contains a photoinitiator.

6. The process of claim 5 wherein the monomeric mesophase contains about 0.5 to about 2.0 weight % photoinitiator.

7. The process of claim 1 wherein the photopolymerizing is initiated by ultraviolet radiation, the monomeric mesophase contains a photoinitiator and the linearly polarized light is laser light having a wavelength within the range of about 400 nm to about 2000 nm.

8. The process of claim 7 wherein the monomeric mesophase contains about 0.5 to about 2.0 weight % of the photoinitiator.

9. The process of claim 8 wherein the photoinitiator is selected from the group consisting of benzophenone, 2,2-dimethoxy-2-phenylacetophenone, 2,2-diethoxyacetophenone, 2-benzoyloxyacetophenone, 2-chlorothioxanthone and 2-hydroxycyclohexyl phenyl ketone.

10. The process of claim 7 wherein the orientation of the mesogens in the at least one region of the monomeric mesophase is induced by a substrate comprising aligned anisotropically absorbing molecules and the orientation of the anisotropically absorbing molecules is induced by the linearly polarized light.

11. The process of claim 10 wherein the substrate comprises a coating containing the anisotropically absorbing molecules.

12. The process of claim 11 wherein the anisotropically absorbing molecules are dichroic dyes.

13. The process of claim 12 wherein the orientation of the mesogens in at least one other region of the monomeric mesophase is induced by surface alignment.

14. The process of claim 12 wherein the dichroic dyes have an absorption bands between about 150 nm and about 2000 nm.

15. The process of claim 13 wherein the dichroic dyes have an absorption bands between about 400 nm and about 2000 nm.

16. The process of claim 4 wherein the orientation of the mesogens in at least one other of the corresponding regions of the monomeric mesophase is induced by surface alignment.

17. The process of claim 1 wherein, the resulting polymeric liquid crystals having aligned multiple oriented mesogens of the general formula:

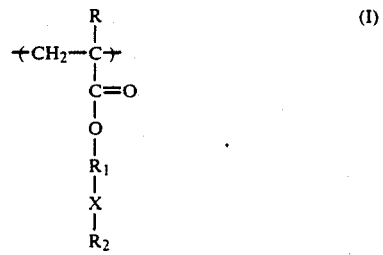

(I)

wherein

R is a hydrogen or CH$_3$;

R$_1$ is a linear or branched C$_2$ to C$_{12}$ alkylene group which is uninterrupted or interrupted by one or more of the groups —O—, —S— or

X is —O—, —S— or

or a covalent bond;

R$_3$ is a C$_1$ to C$_4$ alkyl group;

R$_2$ is a radical of the formula:

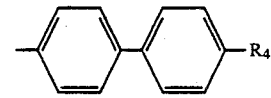

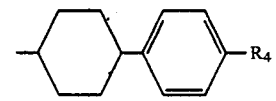

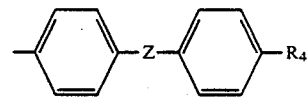

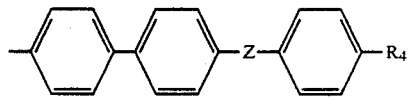

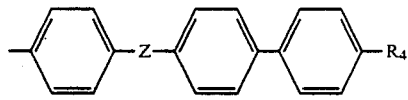

wherein Z is —CO—O—, —O—CO—, —CH=CH—, —N=CH— or —CH=N—; and

R$_4$ is hydrogen, Cl, Br, F, nitro, nitrile, C$_1$ to C$_{12}$ straight chain or branched alkyl, C$_5$ to C$_7$ cycloalkyl, C$_1$ to C$_{12}$ straight chain or branched alkoxy, C$_1$ to C$_{12}$ straight chain or branched alkoxycarbonyl or straight chain or branched alkyl thiolyl.

18. The process of claim 17 wherein the orientation of the mesogens in the at least one region of the monomeric mesophase is induced by a substrate comprising aligned anisotropically absorbing molecules and the anisotropically absorbing molecules are oriented using linearly polarized light, the substrate comprises a coating containing the anisotropically absorbing molecules, and the anisotropically absorbing molecules are dichroic dyes having an absorption bands between about 400 nm and about 2000 nm.

19. The process of claim 18 wherein the photopolymerizing is initiated by ultraviolet radiation, the monomeric mesophase contains about 0.5 to about 2.0 weight % photoinitiator, and the linearly polarized light is laser light having a wavelength within the range of about 400 nm to about 2000 nm.

20. The process of claim 19 wherein the orientation of the mesogens in at least one other of the corresponding regions of the monomeric mesophase is induced by surface alignment.

21. The process of claim 19 wherein the orientation of the mesogens in at least one other of the corresponding regions of the monomeric mesophase is induced by an electric field.

22. The process of claim 19 wherein the orientation of the mesogens in at least one other of the corresponding regions of the monomeric mesophase is induced by a magnetic field.

23. The process of claim 1 wherein the monomeric mesophase is a nematic mesophase.

24. The process of claim 1 wherein the monomeric mesophase is a smectic mesophase.

* * * * *

UNITED STATES PATENT AND TRADEMARK OFFICE
CERTIFICATE OF CORRECTION

PATENT NO. : 5,073,294

DATED : December 17, 1991

INVENTOR(S) : Paul J. Shannon, Shao-Tang Sun and Brian J. Swetlin

It is certified that error appears in the above-identified patent and that said Letters Patent is hereby corrected as shown below:

Col. 6, line 54, after "orientation." insert the following:

" Alignment of a smectic phase in a homogeneous orientation can be accomplished by first aligning the higher temperature nematic phase in a homogeneous orientation using the above mentioned technique, and then cooling the sample into the lower temperature smectic mesophase.

According to a conventional technique for obtaining homeotropic orientation (characterized by the long axis of the liquid crystal aligning along the direction perpendicular to the glass substrate) a glass surface is coated with an orientation layer comprised of polyalkylsiloxanes or lecithins.

Alignment of a nematic phase in a homeotropic orientation can be accomplished by treatment of a glass surface with a polyalkylsiloxane or lecithin coating and curing the coating. Equilibration of a nematic phase between such treated substrates results in a uniformly oriented homeotropic orientation. For instance, orientation of a nematic phase in a homeotropic orientation can easily be accomplished by treatment of a glass substrate with a surface active agent such as n-octadecyldimethyl 3-(trimethoxysilyl)propyl ammonium chloride. Allowing the nematic phase to equilibrate between such treated substrates will result in a uniform homeotropic orientation.

Alignment of a smectic phase in a homeotropic orientation can be accomplished by first aligning the higher temperature nematic phase in a homeotropic orientation using the above mentioned techniques, and then cooling the sample into the lower temperature smectic mesophase.

UNITED STATES PATENT AND TRADEMARK OFFICE
CERTIFICATE OF CORRECTION

PATENT NO. : 5,073,294

DATED : December 17, 1991

INVENTOR(S) : Paul J. Shannon, Shao-Tang Sun and Brian J. Swetlin

It is certified that error appears in the above-identified patent and that said Letters Patent is hereby corrected as shown below:

An applied electric field (applied voltage) or magnetic field can be used to rotate the liquid crystals along a fixed axis so as to alter their properties. For example, a nematic phase possessing positive dielectric anisotropy can be oriented in a homeotropic orientation by an electric field using substrates prepared by coating two pieces of glass with electrically conducting indium-tin oxide. The conducting layers are coated with a layer of polyimide to act as a barrier to charge carriers. Then, the polymerizable nematic material is sandwiched between the treated glass plates, with the conducting layers facing the polymerizable nematic material, and an AC electric field is applied across the nematic layer to generate a uniformly oriented homeotropic orientation. The conducting layers may be applied across the entire useful surface of the glass (the area to be oriented) or selectively coated so that only a portion of the film will be aligned by the electric field.

Similarly, linearly polarized light can be used to rotate anisotropic absorbing molecules which will align the liquid crystals along a fixed axis. The techniques described by Gibbons et al, supra, involve exposing anisotropically absorbing molecules to linearly polarized light of a wavelength or wavelengths within the absorption band of the anisotropically absorbing molecules, wherein the exposed anisotropically absorbing molecules induce orientation of the liquid crystal medium. This process will be referred to as "laser alignment" of liquid crystals since the preferred source of linearly polarized light is a laser.

UNITED STATES PATENT AND TRADEMARK OFFICE
CERTIFICATE OF CORRECTION

PATENT NO. : 5,073,294

DATED : December 17, 1991

INVENTOR(S) : Paul J. Shannon, Shao-Tang Sun and Brian J. Swetlin

It is certified that error appears in the above-identified patent and that said Letters Patent is hereby corrected as shown below:

Laser alignment may be used with liquid crystals monomers adjacent to a substrate (e.g., coated or uncoated glass). The process comprises exposing anisotropically absorbing molecules to linearly polarized light of a wavelength or wavelengths within the absorption band of the anisotropically absorbing molecules. The exposed anisotropically absorbing molecules induce alignment of the liquid crystal monomers at an angle + and - theta with respect to the direction of the linear polarization of the incident light beam.

The anisotropically absorbing molecules preferably form part of the substrate. They are preferably present in a coating adjacent to the liquid crystal medium.

By "anisotropically absorbing molecules" reference is made to compounds which exhibit absorption properties with different values when measured along axes in different directions. Exemplary are liquid crystal compounds and dichroic dyes, with dichroic dyes being most preferred.

Exemplary are dichroic azo, bisazo trisazo, tetrakisazo, pentakisazo, anthraquinone, mericyanine, methine, 2-pheylazothiazole, 2-phenylazobenzthiazole, 4,4'-bis(arylazo)stilbenes, perlyne and 4,8-diamino-1,5-naphtaquinone dyes, and other dyes that exhibit dichroic absorption bands between about 150 nm and about 2000 nm. Due to process constraints described below, in some instances dyes which exhibit dichroic absorption

UNITED STATES PATENT AND TRADEMARK OFFICE
CERTIFICATE OF CORRECTION

PATENT NO. : 5,073,294

DATED : December 17, 1991

INVENTOR(S) : Paul J. Shannon, Shao-Tang Sun and Brian J. Swetlin

It is certified that error appears in the above-identified patent and that said Letters Patent is hereby corrected as shown below:

Col. 14, line 33, under Table 2, insert "Number in parenthesis refers to the cooling cycle."; and Col. 16, line 48, "were" should read "was".

Signed and Sealed this

Sixth Day of July, 1993

Attest:

MICHAEL K. KIRK

Attesting Officer    Acting Commissioner of Patents and Trademarks